United States Patent
Lee et al.

(10) Patent No.: US 11,718,742 B2
(45) Date of Patent: Aug. 8, 2023

(54) SUPERABSORBENT POLYMER COMPOSITION

(71) Applicant: LG Chem, Ltd., Seoul (KR)

(72) Inventors: Jin Woo Lee, Daejeon (KR); Youngsam Kim, Daejeon (KR)

(73) Assignee: LG Chem, Ltd.

( * ) Notice: Subject to any disclaimer, the term of this patent is extended or adjusted under 35 U.S.C. 154(b) by 458 days.

(21) Appl. No.: 16/754,265

(22) PCT Filed: Jan. 9, 2019

(86) PCT No.: PCT/KR2019/000352
§ 371 (c)(1),
(2) Date: Apr. 7, 2020

(87) PCT Pub. No.: WO2019/208905
PCT Pub. Date: Oct. 31, 2019

(65) Prior Publication Data
US 2020/0270441 A1    Aug. 27, 2020

(30) Foreign Application Priority Data

Apr. 27, 2018 (KR) .................. 10-2018-0049252

(51) Int. Cl.
| | | |
|---|---|---|
| *C08L 33/02* | (2006.01) | |
| *B01J 20/26* | (2006.01) | |
| *C08J 3/24* | (2006.01) | |
| *C08K 3/34* | (2006.01) | |
| *C08K 5/00* | (2006.01) | |
| *C08K 5/092* | (2006.01) | |
| *C08K 5/17* | (2006.01) | |

(52) U.S. Cl.
CPC ............. *C08L 33/02* (2013.01); *B01J 20/267* (2013.01); *C08J 3/245* (2013.01); *C08K 3/34* (2013.01); *C08K 5/0058* (2013.01); *C08K 5/092* (2013.01); *C08K 5/175* (2013.01); *B01J 2220/68* (2013.01); *C08K 2201/005* (2013.01)

(58) Field of Classification Search
CPC ......... C08L 33/02; B01J 20/267; C08J 3/245; C08K 3/34; C08K 5/0058; C08K 5/092; C08K 5/175
See application file for complete search history.

(56) References Cited

U.S. PATENT DOCUMENTS

| | | | |
|---|---|---|---|
| 4,990,338 A | 2/1991 | Blank et al. | |
| 6,090,875 A | 7/2000 | Staples et al. | |
| 2003/0135172 A1 | 7/2003 | Whitmore et al. | |
| 2004/0030312 A1 | 2/2004 | Kainth et al. | |
| 2004/0241216 A1 | 12/2004 | Klun et al. | |
| 2006/0025731 A1 | 2/2006 | Cohen | |
| 2006/0183828 A1 | 8/2006 | Dairoku et al. | |
| 2007/0141338 A1* | 6/2007 | Ishizaki | C08J 3/12 502/402 |
| 2009/0299315 A1* | 12/2009 | Flohr | A61L 15/60 604/368 |
| 2018/0043332 A1 | 2/2018 | Lee et al. | |
| 2018/0228670 A1 | 8/2018 | Lee et al. | |
| 2018/0244868 A1 | 8/2018 | Lee et al. | |

FOREIGN PATENT DOCUMENTS

| | | | |
|---|---|---|---|
| CN | 1211265 A | 3/1999 | |
| CN | 107406623 A | 11/2017 | |
| EP | 3375809 A1 | 9/2018 | |
| JP | H08052203 A | 2/1996 | |
| JP | H08243377 A | 9/1996 | |
| JP | H11172129 A | 6/1999 | |
| JP | H11315148 A | 11/1999 | |
| JP | 2003500556 A | 1/2003 | |
| JP | 2004131383 A | 4/2004 | |
| JP | 5903086 B2 | 4/2016 | |
| KR | 101047196 B1 | 7/2011 | |
| KR | 20170068384 A | 6/2017 | |
| KR | 20170075624 A | 7/2017 | |
| KR | 20170106111 A | 9/2017 | |
| KR | 20170136371 A | 12/2017 | |
| WO | 1997030109 A1 | 8/1997 | |
| WO | 2009006377 A1 | 1/2009 | |
| WO | WO-2019206429 A1 * | 10/2019 | ............. A61F 13/47 |

OTHER PUBLICATIONS

Extended European Search Report with Written Opinion for Application No. 19791774.3 dated Nov. 20, 2020, 10 pages.
Chinese Search Report for Application No. 201980005421, dated Jun. 1, 2021, 3 pages.
International Search Report from Application No. PCT/KR2019/000352 dated Apr. 30, 2019, 2 pages.

* cited by examiner

*Primary Examiner* — John E Uselding
(74) *Attorney, Agent, or Firm* — Lerner David LLP

(57) ABSTRACT

A superabsorbent polymer composition exhibiting very improved antimicrobial and deodorizing properties while maintaining basic absorption performance, and can significantly reduce the generation of dust during the application for a process, and thus fulfills both stability and processability and can be usefully applied for hygienic goods such as a diaper and the like. The superabsorbent polymer composition includes: a) superabsorbent polymer particles including a crosslinked polymer of water-soluble ethylenically unsaturated monomers including acid groups, of which at least a part are neutralized, and b) an antimicrobial agent having a controlled particle size, containing a chelating agent including EDTA or an alkali metal salt thereof; a mixture of an organic acid and a silicate-based salt; and an agent for controlling a particle size.

16 Claims, No Drawings

SUPERABSORBENT POLYMER COMPOSITION

CROSS-REFERENCE TO RELATED APPLICATION(S)

The present application is a national stage entry under 35 U.S.C. § 371 of PCT/KR2019/000352 filed on Jan. 9, 2019, which claims priority to Korean Patent Application No. 10-2018-0049252 filed on Apr. 27, 2018 with the Korean Intellectual Property Office, the disclosures of which are herein incorporated by reference in their entirety.

The present invention relates to a superabsorbent polymer composition, and more specifically to a superabsorbent polymer composition that may exhibit improved antimicrobial and deodorizing properties without deterioration of basic absorption performance, and can fulfill both stability and processability.

BACKGROUND ART

A superabsorbent polymer (SAP) is a synthetic polymer material that can absorb moisture of 500 to 1000 times its own weight, and is also called a superabsorbent material (SAM), an absorbent gel material (AGM), etc. according to developing companies. The superabsorbent polymer began to be commercialized for sanitary items, and currently, it is being widely used for hygienic goods such as disposable diapers and the like, water-holding materials for soil, water stop materials for civil engineering and architecture, sheets for raising seedlings, freshness preservatives in the field of food circulation, fomentation materials, and the like, or in the field of electrical insulation.

Such a superabsorbent polymer is most widely applied for hygienic goods or disposable absorption products such as child diapers or adult diapers. Among them, in a case of being applied for adult diapers, secondary odors resulting from bacterial growth gives consumers significant discomfort. In order to solve this problem, there have been attempts to introduce various deodorizing or antimicrobial functional components into a superabsorbent polymer composition before.

However, in the existing attempts to introduce various deodorizing/antimicrobial functional components, even if the superabsorbent polymer exhibits deodorizing/antimicrobial properties, a lot of dust may be generated during the process, thus deteriorating processability and workability. Further, the existing method has disadvantages in that the stability of the superabsorbent polymer may be deteriorated, and the unit cost of a superabsorbent polymer composition may be excessively increased due to the high costs of functional components. Therefore, there is a continued demand for the development of a superabsorbent polymer composition that exhibits more improved antimicrobial and deodorizing properties without deterioration of basic absorption performance, and fulfills both stability and processability as well as excellent economic efficiency.

DISCLOSURE

Technical Problem

It is an object of the present invention to provide a superabsorbent polymer composition that exhibits improved antimicrobial and deodorizing properties without deterioration of basic absorption performance, and particularly, significantly reduces the generation of dust during the process, and thus can fulfill both stability and processability, and hygienic goods including the same.

Technical Solution

The present invention provides a superabsorbent polymer composition including:

a) superabsorbent polymer particles including a cross-linked polymer of water-soluble ethylenically unsaturated monomers including acid groups, of which at least a part are neutralized; and b) an antimicrobial agent having a controlled particle size, containing a chelating agent including EDTA or an alkali metal salt thereof, a mixture of an organic acid and a silicate-based salt, and an agent for controlling a particle size.

The present invention also provides hygienic goods having antimicrobial and deodorizing properties, including the above superabsorbent polymer composition.

Advantageous Effects

According to the superabsorbent polymer composition, a highly improved antimicrobial property to bacteria inducing odor in hygienic goods such as an adult diaper and the like can be provided, and the resulting deodorizing property can be exhibited without deterioration of basic absorption performance such as centrifugal retention capacity, absorbency under pressure, and the like.

Particularly, the present invention provides a method for fulfilling both stability and processability by significantly reducing the generation of dust during the preparation process of a superabsorbent polymer without deterioration of antimicrobial efficiency, even if using an agent for controlling a particle size.

DETAILED DESCRIPTION OF THE EMBODIMENTS

The terms used herein are only to explain specific embodiments, and are not intended to limit the present invention.

A singular expression includes a plural expression thereof, unless it is expressly stated or obvious from the context that such is not intended.

As used herein, the terms "comprise", "have", etc. are intended to designate the existence of a practiced characteristic, number, step, constructional element, or combinations thereof, and they are not intended to preclude the possibility of existence or addition of one or more other characteristics, numbers, steps, constructional elements, or combinations thereof.

Although various modifications can be made to the present invention and the present invention may have various forms, specific examples will be illustrated and explained in detail below.

However, it should be understood that these are not intended to limit the present invention to specific disclosure, and that the present invention includes all the modifications, equivalents, or replacements thereof without departing from the spirit and technical scope of the invention.

Hereinafter, a superabsorbent polymer composition according to specific embodiments of the present invention will be explained in more detail.

A superabsorbent polymer composition according to one embodiment of the invention includes:

a) superabsorbent polymer particles including a cross-linked polymer of water-soluble ethylenically unsaturated monomers including acid groups, of which at least a part are neutralized; and b) an antimicrobial agent having a controlled particle size, containing a chelating agent including EDTA or an alkali metal salt thereof, a mixture of an organic acid and a silicate-based salt, and an agent for controlling a particle size.

First, throughout the specification, the term "antimicrobial agent having a controlled particle size" means an additive performing a function for inhibiting the generation of dust in a process, by increasing the content rate of superabsorbent polymer powders of 150 to 850 μm in the particle size distribution compared to the prior art, by using an agent for controlling a particle size.

That is, by using the antimicrobial agent having a controlled particle size, in the distribution rate of a) powders having a particle size of 850 μm or more, b) powders having a particle size of 600 to 850 μm, c) powders having a particle size of 300 to 600 μm, d) powders having a particle size of 150 to 300 μm, e) powders having a particle size of 45 to 150 μm, and f) powders having a particle size of less than 45 μm, the content rate of superabsorbent polymer powders of 150 to 850 μm may be increased by 10 wt % or more compared to the prior art, and the content of powders having a particle size of less than 150 μm may be decreased. Further, the antimicrobial agent having a controlled particle size means a mixture of three components including a chelating agent including EDTA or an alkali metal salt thereof, a mixture of an organic acid and a silicate-based salt, and an agent for controlling a particle size, which affords an antimicrobial function to the superabsorbent polymer particles.

According to the superabsorbent polymer composition of one embodiment, by using an agent for controlling a particle size in an antimicrobial agent containing a chelating agent including EDTA or an alkali metal salt thereof having a relatively low unit cost, and a mixture of an organic acid and a silicate-based salt, improved deodorizing/antimicrobial properties can be exhibited. Particularly, according to the result of continued experiments by the present inventors, by adding an antimicrobial agent having a controlled particle size obtained by mixing the above-explained three components to superabsorbent polymer particles, the inhibition of growth of bacteria acting as an offensive odor component in an adult diaper and the like can be very effectively inhibited, and simultaneously, dust generated during the application of a process can be significantly reduced. As the result, it was confirmed that the superabsorbent polymer composition of one embodiment may have improved workability and processability without deterioration of excellent antimicrobial and deodorizing properties.

Furthermore, when preparing a superabsorbent polymer having an antimicrobial property, although it is better as the content of an antimicrobial agent is higher, when materials other than the superabsorbent polymer are added, property deterioration may be caused, but in the present invention, due to the use of an optimum amount of an agent for controlling a particle size, dust can be reduced while simultaneously obtaining excellent antimicrobial efficiency. Further, an antimicrobial agent such as a chelating agent added to achieve the antimicrobial property may become a direct cause of dust, but the present invention can remarkably reduce the content of dust in the superabsorbent polymer composition compared to the prior art by adding an antimicrobial agent having a controlled particle size, when compared with the existing antimicrobial agent of the same content.

Thus, the present invention uses an agent for controlling a particle size in an antimicrobial mixture, thereby increasing a particle size and reducing dust, which indicates that the antimicrobial mixture is not eliminated from SAP particles.

In addition, these components do not inhibit the stability of the superabsorbent polymer composition, and thus the superabsorbent polymer composition of one embodiment can maintain excellent basic absorption performance and the unit costs are relatively low, thus largely contributing to the low unit cost and economic efficiency of the superabsorbent polymer composition.

Therefore, the superabsorbent polymer composition of one embodiment can be very preferably applied for various hygienic goods such as an adult diaper and the like.

Hereinafter, each component of the superabsorbent polymer composition of one embodiment will be explained in detail.

The antimicrobial agent for controlling a particle size may be included in a content of 0.1 to 5 parts by weight, based on 100 parts by weight of the sum of the chelating agent, and the mixture of the organic acid and the silicate-based salt.

The superabsorbent polymer composition of one embodiment may include a chelating agent including EDTA or an alkali metal salt thereof, and a mixture of organic acid and a silicate-based salt, so as to achieve unique antimicrobial/deodorizing effects. The chelating agent may include a sodium salt of EDTA-2Na or EDTA-4Na. Further, the chelating agent may further include one or more selected from the group consisting of cyclohexane diamine tetraacetic acid, diethylene triamine pentaacetic acid, ethylene glycol-bis-(aminoethylether)-N,N,N'-triacetic acid, N-(2-hydroxyethyl)-ethylene diamine-N,N,N'-triacetic acid, triethylene tetraamine hexaacetic acid, and alkali metal salts thereof.

Such a chelating agent may exist on the superabsorbent polymer particles to cause a synergistic effect with the mixture of an organic acid and a silicate-based salt, and as the result, the superabsorbent polymer composition of one embodiment may exhibit improved deodorizing/antimicrobial properties.

More specifically, the chelating agent can act as an antimicrobial agent that inhibits the growth rate of various bacteria, particularly, the growth of odor-causing *Proteus mirabilis* bacteria. However, despite the growth inhibition action of the chelating agent, some bacteria may remain, thereby generating offensive odors due to the generation of ammonia and the like. Such odor may be mostly removed by a mixture of an organic acid and a silicate-based salt, and thus the superabsorbent polymer composition of one embodiment may exhibit excellent deodorizing/antibacterial properties by the synergistic effect of two components.

The chelating agent may be included in the content of 0.1 to 5 parts by weight, 0.5 to 3 parts by weight, or 0.9 to 2 parts by weight, based on 100 parts by weight of the superabsorbent polymer particles. By using the chelating agent, the growth rate of odor-causing *Proteus mirabilis* may be appropriately inhibited, and thus an excellent antimicrobial property may be exhibited, and a preferable range of the antimicrobial property (CFU/ml) may be exhibited. Urea is converted into ammonia by *Proteus mirabilis*, and by inhibiting the growth of this bacterium, the amount of ammonia generated may be basically controlled to be low. Thus, the superabsorbent polymer composition of one embodiment may exhibit excellent antimicrobial/deodorizing properties.

However, if the content of the chelating agent becomes too high, even bacteria beneficial to the human body may be removed, or the stability or the absorption property of the superabsorbent polymer may be deteriorated.

Meanwhile, the superabsorbent polymer composition of one embodiment includes a mixture of an organic acid and a silicate-based salt. Such organic acid and silicate-based salt may also exist on the superabsorbent polymer particles.

Such a silicate-based salt may be in the form of a salt in which a silicate anion, and an alkali metal or an alkali earth metal cation, are ionically bonded, and it may exist in the state of particles. Such silicate salt particles may include particles having a particle diameter of 150 μm or more and less than 600 μm in the content of about 80 to about 98 wt %, about 90 to about 99 wt %, or about 92 to about 99.3 wt %.

The organic acid mixed with the silicate-based salt may exist on the superabsorbent polymer particles in the state of particles having a particle diameter of 600 μm or less, or 150 μm to 600 μm.

When the organic acid and silicate-based salt have the above-described particle states and particle size distributions, they may be appropriately maintained on the superabsorbent polymer particles, and thus can more selectively and effectively adsorb bacteria/offensive odor components to physically/chemically remove them. As the result, the superabsorbent polymer of one embodiment may exhibit more improved antimicrobial/deodorizing properties. Furthermore, due to the particle states, when mixed with the superabsorbent polymer, anti-caking performance may be exhibited.

The organic acid may be included in the content of about 90 to 99.5 wt %, about 95 to 99.3 wt %, or about 97 to 99.0 wt %, based on the total weight of the mixture of an organic acid and a silicate-based salt. Thus, inside and/or on the surface of the superabsorbent polymer particles, a large number of acid sites may be generated. If such acid sites are included, various offensive odor components may be physically adsorbed, and the hydrogen cations (H+) of the acid sites may bond with offensive odor components to form ammonium salts, thereby more effectively removing offensive odor components.

The organic acid may include one or more selected from the group consisting of citric acid, fumaric acid, maleic acid, and lactic acid, but it is not limited thereto.

According to one embodiment of the invention, the mixture of an organic acid and a silicate-based salt may be included in the content of about 0.5 to about 5 parts by weight, about 0.8 to about 5 parts by weight, or about 1 to about 4 parts by weight, based on 100 parts by weight of the superabsorbent polymer. If the contents of these components are too small, deodorizing property obtained by the organic acid and the like may not be sufficient, and if the contents are too large, the properties of the superabsorbent polymer may be deteriorated.

The mixture of an organic acid and a silicate-based salt may be prepared by a common method of mixing the organic acid and the silicate-based salt. Although such a mixture may be prepared by previously mixing these two components, each component may be mixed with a chelating agent after preparing superabsorbent polymer particles, as described below.

Meanwhile, in the present invention, an antimicrobial agent exhibiting antimicrobial/deodorizing effects is prepared through mixing of the above-explained three components, and an agent for controlling a particle size is added, thereby controlling the particle size of superabsorbent polymer particles, thus significantly reducing the generation of dust in the preparation process of the superabsorbent polymer.

That is, the conventional antimicrobial agent has a problem in that particles of #100 or less (150 μm or less) occupy 18.35 wt % and thus a lot fine dust is generated while mixing with the superabsorbent polymer. However, according to the present invention, by adding an agent for controlling a particle size to the chelating agent and the mixture of organic acid and silicate-based salt, particles of #100 or less (150 μm or less) exist in the content of 0.5 wt % or less, or preferably 0.1 wt % or less. Thus, the present invention can improve processability and workability, and simultaneously increase the content rate of superabsorbent polymer powders of 150 to 850 μm compared to the prior art.

Therefore, in the present invention, by using an agent for controlling a particle size, the particle size distribution range of 150 to 850 μm may be increased.

Herein, the agent for controlling a particle size may be included in the content of 0.5 to 5 parts by weight, based on 100 parts by weight of the sum of the chelating agent and the mixture of organic acid and silicate-based salt. If the content of the agent for controlling a particle size is less than 0.5 parts by weight, there may be no dust decreasing effect, and if it is greater than 5 parts by weight, properties may be significantly deteriorated.

The agent for controlling a particle size may be one or more selected from the group consisting of mineral oil, natural oil, baby oil, corn oil, olive oil, and silicone oil. According to one preferable embodiment, the agent for controlling a particle size may be mineral oil.

In the present invention, by using the agent for controlling a particle size in an antimicrobial mixture, excellent antimicrobial efficiency may be maintained, a particle size may be increased, and the amount of dust generation, which can determine whether or not the antimicrobial mixture is eliminated from SAP particles, may be reduced.

The antimicrobial agent having a controlled particle size may be included in the content of 0.1 to 5 parts by weight, based on 100 parts by weight of the superabsorbent polymer particles. Preferably, when the antimicrobial agent having a controlled particle size is included in the content of 1 to 4 parts by weight based on 100 parts by weight of the superabsorbent polymer particles, the particle size distribution of #100 or less (150 μm or less) may become 0 to less than 1.5 wt % based on the total weight, thereby more effectively reducing the generation of fine dust, and the content rate of the superabsorbent polymer powders of 150 to 850 μm may be increased to more than in the prior art. If the content of the antimicrobial agent having a controlled particle size is less than 0.1 parts by weight, there may be no antimicrobial effect, and if it is greater than 5 parts by weight, properties may be significantly deteriorated.

Thus, in the superabsorbent polymer composition of one embodiment, the above-explained antimicrobial agent having a controlled particle size may exist on the superabsorbent polymer particles.

Meanwhile, the kind or preparation method of the superabsorbent polymer that is mixed with the antimicrobial agent having a controlled particle size, which is a mixture of the above-explained three components, may be those commonly used in the art, and the steps and methods of mixing these components with the superabsorbent polymer are not specifically limited.

For example, the superabsorbent polymer may be obtained by progressing thermal polymerization or photo-polymerization of a monomer composition including water soluble ethylenically unsaturated monomers and a polymerization initiator to obtain a hydrogel polymer, and drying, grinding, sieving, and if necessary, surface crosslinking or fine powder reassembly processing it, and the like, may be further conducted.

For reference, throughout the specification, "superabsorbent polymer" means to include a crosslinked polymer in which water-soluble ethylenically unsaturated monomers including acid groups, of which at least a part are neutralized, are polymerized; a base polymer made in the form of a powder by drying and grinding the crosslinked polymer; or those made suitable for the productization by subjecting the crosslinked polymer or base polymer to additional processes, for example, surface crosslinking, fine powder reassembly, drying, grinding, sieving, and the like, according to the context.

As the water-soluble ethylenically unsaturated monomers, any monomers commonly used for the preparation of a superabsorbent polymer may be used without specific limitations. As the water-soluble ethylenically unsaturated monomers, one or more monomers selected from the group consisting of anionic monomers and salts thereof, non-ionic hydrophilic group-containing monomers, amino group-containing unsaturated monomers, and quaternarized products thereof, may be used.

Specifically, one or more selected from the group consisting of anionic monomers and salts thereof such as acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloyl propane sulfonic acid, or 2-(meth)acrylamid-2-methyl propane sulfonic acid; non-ionic hydrophilic group-containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group-containing unsaturated monomers such as (N,N)-dimethylaminoethyl (meth)acrylate, (N,N)-dimethylaminopropyl (meth)acrylamide, and quaternarized products thereof, may be used.

More preferably, as the water soluble ethylenically unsaturated monomers, acrylic acid, or salts thereof, for example, acrylic acid or an alkali metal salt such as a sodium salts thereof may be used, and in case such monomers are used, a superabsorbent polymer having excellent properties can be prepared. In case an alkali metal salt of acrylic acid is used as the water soluble ethylenically unsaturated monomers, acrylic acid may be neutralized with a basic compound such as caustic soda (NaOH) before use.

A polymerization initiator that is used when polymerizing the water-soluble ethylenically unsaturated monomers is not specifically limited as long as it is commonly used for the preparation of a superabsorbent polymer.

Specifically, as the polymerization initiator, a thermal polymerization initiator or a photopolymerization initiator by UV irradiation may be used according to a polymerization method. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

According to one embodiment of the invention, the monomer composition may further include an internal crosslinking agent as the raw material of the superabsorbent polymer.

As the internal crosslinking agent, a crosslinking agent having one or more functional groups capable of reacting with the water soluble substituents of the water soluble ethylenically unsaturated monomers, and having one or more ethylenically unsaturated groups; or a crosslinking agent having two or more functional groups capable of reacting with the water soluble substituents of the monomers and/or the water soluble substituents formed by the hydrolysis of the monomers, may be used.

As specific examples of the internal crosslinking agent, C8-12 bisacrylamide, bismethacrylamide, C2-10 polyol poly(meth)acrylate, C2-10 polyol poly(meth)allylether, and the like may be mentioned, and more specifically, one or more selected from the group consisting of N,N'-methylene bis(methacrylate), ethylene oxy(methacrylate), polyethylene oxy(methacrylate), propylene oxy(methacrylate), glycerin diacrylate, glycerin triacrylate, trimethylol triacrylate, triallyl amine, triaryl cyanurate, triallyl isocyanate, polyethylene glycol, diethylene glycol, and propylene glycol may be used.

In the preparation method, the monomer composition may further include additives such as a thickener, a plasticizer, a preservation stabilizer, an antioxidant, etc., as necessary.

The above-explained raw materials such as water soluble ethylenically unsaturated monomers, a photopolymerization initiator, a thermal polymerization initiator, an internal crosslinking agent, and additives may be prepared in the form of a solution dissolved in a solvent.

Meanwhile, a method of forming a hydrogel polymer by the thermal polymerization or photopolymerization of the monomer composition is not specifically limited in terms of its construction, as long as it is a commonly used polymerization method.

Specifically, the polymerization method is largely classified into thermal polymerization and photopolymerization according to an energy source. Commonly, thermal polymerization may be progressed in a reactor equipped with a stirring axis such as a kneader, and photopolymerization may be progressed in a reactor equipped with a movable conveyer belt, but the above-explained polymerization methods are no more than examples, and the present invention is not limited thereto.

Here, the moisture content of hydrogel polymer obtained by such a method may be about 40 to about 80 wt %. Throughout the specification, the "moisture content" is the content of moisture occupied based on the total weight of the hydrogel polymer, and it means a value obtained by subtracting the weight of the polymer in a dry state from the weight of hydrogel polymer. Specifically, it is defined as a value calculated by measuring the weight loss according to moisture evaporation in the polymer while raising the temperature of the polymer through infrared heating to dry it. At this time, the drying condition is set such that the temperature is raised from room temperature to about 180° C. and then maintained at 180° C., and the total drying time is 20 minutes including a temperature raising step of 5 minutes.

Next, the obtained hydrogel polymer is dried.

Herein, a coarse grinding step may be further conducted before drying the hydrogel polymer so as to increase drying efficiency.

Here, grinders that can be used in the coarse grinding are not limited in terms of their constructions, but specifically, one selected from the group consisting of a vertical pulverizer, a turbo cutter, a turbo grinder, a rotary cutter mill, a cutter mill, a disc mill, a shred crusher, a crusher, a chopper, and a disc cutter may be used, but the grinder is not limited thereto.

Through the coarse grinding step, the particle diameter of the hydrogel polymer may be controlled to about 2 to about 10 mm.

The hydrogel polymer coarsely ground as explained above, or the hydrogel polymer immediately after polymerization that is not subjected to the coarse grinding step, is dried.

The drying method is not limited in terms of the construction as long as it is commonly used as a drying process of a hydrogel polymer. Specifically, the drying step may be progressed by hot wind supply, infrared ray irradiation, ultrahigh frequency wave irradiation, UV irradiation, etc. The polymer dried by such a method may exhibit a moisture content of about 0.1 to about 10 wt %.

Next, the dried polymer obtained through the drying step is ground.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, a jog mill, etc. may be used, but the grinder is not limited thereto.

In order to manage the properties of the superabsorbent polymer powders finally productized after the grinding step, the polymer powders obtained after grinding may be subjected to a separate process of sieving according to the particle diameter. Preferably, polymer powders having a particle diameter of about 150 to about 850 μm are sieved.

According to one embodiment of the invention, the ground or sieved polymer may be subjected to a step of surface crosslinking. Herein, the surface crosslinking agent is not limited in terms of its construction as long as it can react with the functional group of the polymer. As examples of the surface crosslinking agent, polyhydric alcohol compounds, multivalent alkylene carbonate compounds, multivalent epoxy compounds, and the like may be mentioned.

The surface crosslinking agent may be included in the content of about 0.01 to 5 parts by weight, based on 100 parts by weight of the base polymer powder obtained from the ground or sieved polymer.

When the surface crosslinking agent is used, it may further include water and/or methanol.

The surface crosslinking step may be conducted by heating at a temperature of 140 to 200° C. for 5 to 80 minutes. Preferably, the base polymer powder to which the surface crosslinking solution is added may be heated at a maximum reaction temperature of 140° C. to 200° C., or 150° C. to 190° C., for 5 to 80 minutes, 10 to 70 minutes, or 20 to 65 minutes, thus progressing a surface crosslinking reaction. More specifically, the surface crosslinking step may be progressed by raising the temperature from the initial temperature of 20° C. to 130° C., or 40° C. to 120° C., to the maximum reaction temperature for 10 to 40 minutes, and maintaining the maximum temperature for 5 to 80 minutes, thus heat treating.

A temperature rise means for the surface crosslinking reaction is not specifically limited. A heating medium may be supplied, or a heat source may be directly supplied to heat it. Here, the kinds of the heating medium that can be used may include a temperature-increased fluid such as steam, hot air, hot oil, etc., but is not limited thereto, and the temperature of the heating medium supplied may be appropriately selected considering the means of the heating medium, temperature rise speed, and a temperature to be increased. Meanwhile, for the heat source directly supplied, electric heating, gas heating, etc., may be used, but is not limited thereto.

Thus, according to the present invention, a superabsorbent polymer composition further including a surface crosslink layer formed on the superabsorbent polymer particles may be provided.

The superabsorbent polymer particles obtained by the above process, the above-explained chelating agent, and the mixture of an organic salt and a silicate-based salt may be uniformly mixed to obtain the superabsorbent polymer composition of one embodiment of the present invention.

Herein, a method of mixing is not specifically limited, and for example, superabsorbent polymer particles, a chelating agent, an organic acid, and a silicate salt may be put into a reactor and mixed; a solution including a chelating agent, an organic acid, and a silicate salt may be sprayed to the superabsorbent polymer; a superabsorbent polymer, a chelating agent, an organic acid, and silicate salt particles may be continuously fed into a reactor such as a continuously operated mixer and mixed; or an organic acid and a silicate salt may be previously mixed, and then a superabsorbent polymer, a chelating agent, and the mixture of an organic acid and a silicate salt may be continuously fed and mixed.

Meanwhile, in the superabsorbent polymer composition of one embodiment, the superabsorbent polymer particles may further include residual iron ions derived from a monomer composition including water soluble ethylenically unsaturated monomers and/or an initiator, in the content of 3 ppmw or less, or 0.1 to 3 ppmw, based on the total monomers.

In the preparation process of superabsorbent polymer particles, a polymerization initiator such as a common redox initiator and the like may be used, and iron ions derived from the initiator may remain in the monomers and/or superabsorbent polymer particles. However, such iron ions may cause property deterioration of a superabsorbent polymer composition, but since the composition of one embodiment includes a chelating agent, the remaining amount of the iron ions may be reduced. As a result, the superabsorbent polymer composition of one embodiment may exhibit excellent properties.

Meanwhile, a method of preparing a superabsorbent polymer composition having an antimicrobial property may include steps of: mixing a certain amount of a chelating agent including EDTA or an alkali metal salt thereof; mixing an organic acid and a silicate-based salt and an agent for controlling a particle size to prepare an antimicrobial agent having a controlled particle size; and mixing superabsorbent polymer particles and the antimicrobial agent having a controlled particle size.

Herein, an apparatus for preparing the antimicrobial agent having a controlled particle size and antimicrobial superabsorbent polymer particles is not particularly limited in terms of its constructions and conditions, and they may be prepared through stirring using a common mixer (for example, a Ploughshare blender).

The superabsorbent polymer composition of one embodiment obtained as explained above may exhibit excellent antimicrobial/deodorizing effects and basic absorption properties.

Further, the final antimicrobial superabsorbent polymer composition to which an antimicrobial agent having a controlled particle size prepared by mixing the above-explained four components is added may be in the form of particles having an average particle size of 150 to 850 μm. That is, in the present invention, by significantly reducing the fine particles in the particle size distribution of an antimicrobial agent, the content of fine particles in the total superabsorbent polymer composition may also be reduced, and particularly, a particle size distribution of 150 to 850 μm may be increased. Particularly, an antimicrobial agent such as a chelating agent that is added to exhibit the antimicrobial property may become a direct cause of fine particles, but in the present invention, by adding an antimicrobial agent having a controlled particle size, the content of fine particles in the superabsorbent polymer composition may be significantly reduced, compared to the conventional antimicrobial agent of the same content.

Preferably, in the total particle size distribution of the superabsorbent polymer composition of the present invention, the rate of particles having an average particle size of 150 to 850 μm obtained by sieving may be 99 wt % or more, preferably 99.1 wt % or more. Herein, since the superabsorbent polymer composition basically includes fine particles of the superabsorbent polymer itself, when the antimicrobial agent is included, the fine particles of the superabsorbent polymer itself may also be included. More preferably, in the total particle size distribution of the superabsorbent polymer composition of the present invention, the rate of absorbent polymer powders having a particle size of less than 150 μm may be 1.5 wt % or less, and the rate of absorbent polymer powders having a particle size of 850 μm or more may be 1 wt % or 0.8 wt % or less. Herein, in the rate of the superabsorbent polymer powders having a particle size of less than 150 μm, the rate of the superabsorbent polymer powders having an average particle size of less than 45 μm may be 0.5 wt % or less, 0.05 wt % or less, or 0 wt %, and the rate of the superabsorbent polymer powders of 45 to 150 μm may be 1 wt % or less or 0.5 wt % or less. More preferably, in the average particle size distribution measured with a standard sieve, based on the total powder content, a) the rate of powders having an average particle size of 850 μm or more may be 1 wt % or less, b) the rate of powders having a particle size of 600 to 850 μm may be 15~18 wt %, c) the rate of powders having a particle size of 300 to 600 μm may be 59~63 wt %, d) the rate of powders having a particle size of 150 to 300 μm may be 19~23 wt %, e) the rate of powders having a particle size of 45 to 150 μm may be 0.5 wt % or less, and f) the rate of powders having a particle size of less than 45 μm may be 0.5 wt % or less.

Meanwhile, according to another embodiment of the present invention, hygienic goods having excellent antimicrobial/deodorizing effects may be provided by a method having excellent processability and stability.

That is, the present invention provides antimicrobial, deodorizing hygienic goods including the superabsorbent polymer composition. The hygienic goods include disposable absorption products, and preferably include diapers, which may be child diapers or adult diapers. The hygienic goods can improve a sense of use due to excellent antimicrobial and deodorizing properties as explained above, while maintaining basic absorption properties such as centrifugal retention capacity and absorption under pressure, and the like.

Hereinafter, the actions and the effects of the invention will be explained in more detail, through specific examples of the invention.

However, these examples are presented only as illustrations of the invention, and the scope of the right of the invention is not limited thereby.

EXAMPLE

Example: Preparation of a Superabsorbent Polymer Composition

Example 1

100 parts by weight of acrylic acid monomers were mixed with 38.9 parts by weight of caustic soda (NaOH) and 103.9 parts by weight of water, and to the mixture, 0.1 parts by weight of a thermal polymerization initiator of sodium persulfate, 0.01 parts by weight of a photopolymerization initiator of diphenyl(2,4,6-trimethylbenzoyl)phosphine oxide, and 0.3 parts by weight of a crosslinking agent of polyethylene glycol diacrylate were added to prepare a monomer composition.

While the monomer composition was flowed at the flow rate of 243 kg/h on a polymerization belt of a continuous belt polymerization reactor, of which internal temperature is maintained at 80° C., and on top of which a UV irradiation device having intensity of 10 mW with a mercury UV lamp light source is installed, UV was irradiated for 1 minute, and a polymerization reaction was progressed for an additional 2 minutes without a light source.

A gel type of polymerization sheet emerging after the polymerization was finished was primarily cut using a shredder type of cutter, and then coarsely ground through a meat chopper. Thereafter, it was dried at 180° C. for 30 minutes through a hot air dryer, and then ground using a rotary mixer and sieved to 150 μm to 850 μm, thus preparing a base polymer.

Into the base polymer, 0.1 wt % of ethylene glycol diglycidyl epoxide were introduced and uniformly mixed, and then a surface treatment was progressed at 140° C. for 1 hour to obtain a superabsorbent polymer.

Based on 100 parts by weight of the superabsorbent polymer, i) 0.5 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 0.25 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size, and the particle size distribution of the antimicrobial agent is as follows.

That is, in the average particle size distribution measured with a standard sieve, based on the total powder content, a) the rate of powders having an average particle size of 850 μm or more was 0.8 wt %, b) the rate of powders having a particle size of 600 to 850 μm was 16.6 wt %, c) the rate of powders having a particle size of 300 to 600 μm was 60.9 wt %, d) the rate of powders having a particle size of 150 to 300 μm was 21.6 wt %, e) the rate of powders having a particle size of 45 to 150 μm was 0.1 wt %, and f) the rate of powders having a particle size of less than 45 μm was 0 wt %.

Apparatuses and Reagents

Electronic scale (precision: 0.01 g), sieve shaker, sieve (20, 30, 50, 100, 325 mesh standard sieve), pan receiver and cap, 250 ml beaker Test Method A pan receiver was placed on the lowest stage, and sieves were sequentially stacked thereon from the sieve having the smallest mesh size. 100 g of the sample was quantitatively weighed in a 250 ml beaker, and then put in the highest stage sieve, and the lid was closed. The sieve apparatus was fixed in a sieve shaker, and shaken for 10 minutes. After shaking for 10 minutes, the samples remaining on each sieve wire mesh were collected and weighed. At this time, care was taken so that the samples were not spilled to the outside, and the measurement width was set up as 1.0 mm.

Calculation Method

The rate remaining on the sieves was calculated by the following Equation 1.

The rate remaining on each sieve (%)=(the weight of the sample remaining on each sieve/total sample weight)×100 [Equation 1]

Report

Particles of 20 mesh or larger, 20 to 30 mesh, 30 to 50 mesh, 50 to 100 mesh, 100 to 325 mesh, and 325 mesh or smaller were measured.

Herein, the particle sizes were reported in a data sheet to two decimal point, while the particle size of "325 mesh or smaller" was rounded off to a significant figure.

Thereafter, 100 parts by weight of the superabsorbent polymer and 2.52 parts by weight of the antimicrobial agent having a controlled particle size were mixed, and the prepared superabsorbent polymer composition was referred to as Example 1. Further, based on the total content of the superabsorbent polymer composition (superabsorbent polymer+antimicrobial agent having a controlled particle size), the rate of superabsorbent polymer particles of 150 μm to less than 850 μm was 97 wt % or more, the rate of superabsorbent polymer particles of 45 μm to less than 150 μm was 1.5 wt % or less, the rate of superabsorbent polymer particles of less than 45 μm was 0 wt %, and the rate of superabsorbent polymer particles of 850 μm or more was 1.0 wt % or less.

For the antimicrobial agent containing EDTA-2Na in the low content of 0.5 parts by weight, or 0.8 parts by weight, only a dust generation tendency according to an increase in the content of mineral oil was observed, and the antimicrobial efficiency was measured when the EDTA-2Na content was 1.0 part by weight (phr). The PSD of the final antimicrobial SAP was also measured only at that time.

Example 2

A superabsorbent polymer was prepared by the same method as Example 1.

Based on 100 parts by weight of the superabsorbent polymer, i) 0.5 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 0.5 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size, and the particle size distribution of the antimicrobial agent is the same as Example 1.

Thereafter, 100 parts by weight of the superabsorbent polymer and 2.52 parts by weight of the antimicrobial agent having a controlled particle size were mixed, and the prepared superabsorbent polymer composition is referred to as Example 2.

Example 3

A superabsorbent polymer was prepared by the same method as Example 1.

Based on 100 parts by weight of the superabsorbent polymer, i) 0.5 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 1 part by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1.

Thereafter, 100 parts by weight of the superabsorbent polymer and 2.52 parts by weight of the antimicrobial agent having a controlled particle size were mixed, and the prepared superabsorbent polymer composition is referred to as Example 3.

Example 4

A superabsorbent polymer was prepared by the same method as Example 1.

Based on 100 parts by weight of the superabsorbent polymer, i) 0.5 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 1.5 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1.

Thereafter, 100 parts by weight of the superabsorbent polymer and 2.52 parts by weight of the antimicrobial agent having a controlled particle size were mixed, and the prepared superabsorbent polymer composition is referred to as Example 4.

Example 5

A superabsorbent polymer was prepared by the same method as Example 1.

Based on 100 parts by weight of the superabsorbent polymer, i) 0.8 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 0.5 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1

Thereafter, 100 parts by weight of the superabsorbent polymer and 2.82 parts by weight of the antimicrobial agent having a controlled particle size were mixed, and the prepared superabsorbent polymer composition is referred to as Example 5.

Example 6

A superabsorbent polymer was prepared by the same method as Example 1.

Based on 100 parts by weight of the superabsorbent polymer, i) 0.8 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 1 part by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1

Thereafter, 100 parts by weight of the superabsorbent polymer and 2.82 parts by weight of the antimicrobial agent having a controlled particle size were mixed, and the prepared superabsorbent polymer composition is referred to as Example 6.

Example 7

A superabsorbent polymer was prepared by the same method as Example 1.

Based on 100 parts by weight of the superabsorbent polymer, i) 0.8 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 1.5 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1

Thereafter, 100 parts by weight of the superabsorbent polymer and 2.82 parts by weight of the antimicrobial agent having a controlled particle size were mixed, and the prepared superabsorbent polymer composition is referred to as Example 7.

Example 8

A superabsorbent polymer was prepared by the same method as Example 1.

Based on 100 parts by weight of the superabsorbent polymer, i) 0.8 parts by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 2 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1.

Thereafter, 100 parts by weight of the superabsorbent polymer and 2.82 parts by weight of the antimicrobial agent having a controlled particle size were mixed, and the prepared superabsorbent polymer composition is referred to as Example 8.

Example 9

A superabsorbent polymer was prepared by the same method as Example 1.

Based on 100 parts by weight of the superabsorbent polymer, i) 1 part by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 0.125 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1

Thereafter, 100 parts by weight of the superabsorbent polymer and 3.02 parts by weight of the antimicrobial agent having a controlled particle size were mixed, and the prepared superabsorbent polymer composition is referred to as Example 9.

Example 10

A superabsorbent polymer was prepared by the same method as Example 1.

Based on 100 parts by weight of the superabsorbent polymer, i) 1 part by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 0.25 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1

Thereafter, 100 parts by weight of the superabsorbent polymer and 3.02 parts by weight of the antimicrobial agent having a controlled particle size were mixed, and the prepared superabsorbent polymer composition is referred to as Example 10.

Example 11

A superabsorbent polymer was prepared by the same method as Example 1.

Based on 100 parts by weight of the superabsorbent polymer, i) 1 part by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 0.5 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1.

Thereafter, 100 parts by weight of the superabsorbent polymer and 3.02 parts by weight of the antimicrobial agent having a controlled particle size were mixed, and the prepared superabsorbent polymer composition is referred to as Example 11.

Example 12

A superabsorbent polymer was prepared by the same method as Example 1.

Based on 100 parts by weight of the superabsorbent polymer, i) 1 part by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 1 part by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1.

Thereafter, 100 parts by weight of the superabsorbent polymer and 3.02 parts by weight of the antimicrobial agent having a controlled particle size were mixed, and the prepared superabsorbent polymer composition is referred to as Example 12.

Example 13

A superabsorbent polymer was prepared by the same method as Example 1.

Based on 100 parts by weight of the superabsorbent polymer, i) 1 part by weight of EDTA sodium salt (EDTA-2Na) and ii) 2.02 parts by weight of a mixture including 99 wt % of citric acid and 1 wt % of sodium metasilicate salt, and iii) based on 100 parts by weight of the mixture of i) and ii), 2 parts by weight of mineral oil, which is an agent for controlling a particle size, were put in a Ploughshare blender, followed by stirring at 500 rpm for 5 minutes. The prepared mixture of three components is referred to as an antimicrobial agent having a controlled particle size. The particle size distribution of the antimicrobial agent is the same as Example 1

Thereafter, 100 parts by weight of the superabsorbent polymer and 3.02 parts by weight of the antimicrobial agent having a controlled particle size were mixed, and the prepared superabsorbent polymer composition is referred to as Example 13.

Based on the total content of the antimicrobial superabsorbent polymer composition including an antimicrobial agent having a controlled particle size (superabsorbent polymer+antimicrobial agent having a controlled particle size), the rate of superabsorbent polymer particles of 150 μm to less than 850 μm was 97 wt % or more, the rate of superabsorbent polymer particles of 45 μm to less than 150 μm was 1.5 wt % or less, the rate of superabsorbent polymer particles of less than 45 μm was 0 wt %, and the rate of superabsorbent polymer particles of 850 μm or more was 1.0 wt % or less.

Comparative Example 1

A superabsorbent polymer was prepared by the same method as Example 1.

Based on 100 parts by weight of the superabsorbent polymer, i) 0.25 parts by weight of EDTA sodium salt (EDTA-2Na) and ii) 2.02 parts by weight of a mixture including 99 wt % of citric acid and 1 wt % of sodium metasilicate salt were put in a Ploughshare blender, followed by stirring at 500 rpm for 2 minutes.

Thereafter, 100 parts by weight of the superabsorbent polymer and 2.27 parts by weight of the mixture of two components as prepared above were mixed, and the prepared superabsorbent polymer composition is referred to as Comparative Example 1.

The antimicrobial mixture without mineral oil had a particle size distribution wherein the rate of particles of 150 μm to less than 850 μm was 82 wt % or less, the rate of particles of 45 μm to less than 150 μm was 13~15 wt %, the rate of particles of less than 45 μm was 4~6 wt %, and the rate of particles of 850 μm or more was 0.5 wt % or less.

Comparative Example 2

A superabsorbent polymer was prepared by the same method as Example 1.

Based on 100 parts by weight of the superabsorbent polymer, i) 0.5 parts by weight of EDTA sodium salt (EDTA-2Na) and ii) 2.02 parts by weight of a mixture including 99 wt % of citric acid and 1 wt % of sodium metasilicate salt were put in a Ploughshare blender, followed by stirring at 500 rpm for 2 minutes.

Thereafter, 100 parts by weight of the superabsorbent polymer and 2.52 parts by weight of the mixture of two components as prepared above were mixed, and the prepared superabsorbent polymer composition is referred to as Comparative Example 2.

The antimicrobial mixture without mineral oil had the same particle size distribution as Comparative Example 1.

Comparative Example 3

A superabsorbent polymer was prepared by the same method as Example 1.

Based on 100 parts by weight of the superabsorbent polymer, i) 1 part by weight of EDTA sodium salt (EDTA-2Na) and ii) 2.02 parts by weight of a mixture including 99 wt % of citric acid and 1 wt % of sodium metasilicate salt were put in a Ploughshare blender, followed by stirring at 500 rpm for 2 minutes.

Thereafter, 100 parts by weight of the superabsorbent polymer and 3.02 parts by weight of the mixture of two components as prepared above were mixed, and the prepared superabsorbent polymer composition is referred to as Comparative Example 3.

The antimicrobial mixture without mineral oil had the same particle size distribution as Comparative Example 1.

Based on the total content of the antimicrobial superabsorbent polymer composition including an antimicrobial mixture of which particle size was not controlled (superabsorbent polymer+antimicrobial agent of which particle size was not controlled), the rate of superabsorbent polymer particles of 150 μm to less than 850 μm was 97 wt % or less, the rate of superabsorbent polymer particles of 45 μm to less than 150 μm was 1.5~3 wt %, the rate of superabsorbent polymer particles of less than 45 μm was 0.2~1.0 wt %, and the rate of superabsorbent polymer particles of 850 μm or more was 0.5 wt % or less.

Reference Example 1 i) 1 part by weight of EDTA sodium salt (EDTA-2Na) and ii) 2.02 parts by weight of a mixture including 99 wt % of citric acid and 1 wt % of sodium metasilicate salt were put in a Ploughshare blender, followed by stirring at 500 rpm for 2 minutes. The prepared mixture was used to as an antimicrobial agent, and is referred to as Reference Example 1.

Reference Example 2 i) 0.5 parts by weight of EDTA sodium salt (EDTA-2Na) and ii) 2.02 parts by weight of a mixture including 99 wt % of citric acid and 1 wt % of sodium metasilicate salt were put in a Ploughshare blender, followed by stirring at 500 rpm for 2 minutes. The prepared mixture was used to as an antimicrobial agent, and is referred to as Reference Example 2.

Both the antimicrobial mixture of Reference Examples 1 and 2 exhibited a) the rate of powders having a particle size of 850 µm or more of 0.5 wt % or less, b) the rate of powders having a particle size of 600 to 850 µm of 13~16 wt %, c) the rate of powders having a particle size of 300 to 600 µm of 35~38 wt %, d) the rate of powders having a particle size of 150 to 300 µm of 26~29 wt %, e) the rate of powders having a particle size of 45 to 150 µm of 12~14 wt %, and f) the rate of powders having a particle size of less than 45 µm of 4~6 wt %, based on the total powder content, in the average particle size distribution measured with a standard sieve.

Evaluation of the Properties of Superabsorbent Polymer

The properties of the superabsorbent polymer compositions of Examples 1 to 13 and Comparative Examples 1 to 3 were measured as follows, and the results are shown in Tables 1 and 2.

(1) Antimicrobial/Deodorizing Performance Test 50 ml of artificial urine inoculated with 250,000 CFU/ml of *Proteus mirabillis* (ATCC 29906) was incubated in an oven of 35° C. for 12 hours. The artificial urine and the artificial urine after incubation for 12 hours were referred to as controls, and were properly washed with 150 ml of a saline solution to measure CFUs (colony forming units), thereby calculating the properties of the controls.

Two grams of each of the superabsorbent polymer, and the superabsorbent polymer compositions of Example 9 to 13 and Comparative Examples 1 to 3, were put into 50 ml of the artificial urine inoculated with 250,000 CFU/ml of *Proteus mirabillis* (ATCC 29906), followed by shaking for 1 minute to uniformly mix them. Thereafter, it was incubated in an oven of 35° C. for 12 hours. The artificial urine after incubation for 12 hours was properly washed with 150 ml of a saline solution to measure CFUs (colony forming units). Thereby, the antimicrobial/deodorizing properties of each example and comparative example were calculated/evaluated.

(2) Measurement of DUST Value

A DUST value was analyzed using Dustview II equipment (manufactured by Palas GmbH) capable of measuring the degree of dust of the superabsorbent polymer with a laser.

A dust number was measured using 30 g of the SAP sample prepared in the examples or comparative examples, and since small particles and specific materials drop at lower speeds than bigger grains, a dust number was calculated by the following Equation 2.

$$\text{Dust number} = \text{Max value} + 30s \text{ value} \quad [\text{Equation 2}]$$

(In Equation 2, Max value denotes the maximum dust value, and the 30 s value denotes a value measured 30 seconds after reaching the maximum dust value.)

(3) Flowability

The superabsorbent polymer prepared in the examples or comparative examples was properly mixed so that particles may be uniformly mixed, and then 100±0.5 g of each sample was taken and poured into a 250 ml beaker. On the bottom of a funnel having the lowest stage diameter of 1 cm (unit), a cup for measuring density was positioned right at the center, and then the hole of the funnel was blocked and the metered sample was lightly poured into the funnel and filled. At the moment when the blocked hole of the funnel was opened, a stop watch was operated to measure a time (seconds) taken until the sample completely went down to the lowest stage part of the funnel. All the processes were progressed in a constant temperature and constant humidity chamber (temperature 23±2° C., relative humidity 45±10%).

(4) Bulk Density 100 g of each superabsorbent polymer was flowed through the orifice of an apparatus for measuring standard fluidity and received in a container having a volume of 100 ml, and the superabsorbent polymer was planed so as to become horizontal, thus controlling the volume of the superabsorbent polymer to 100 ml, and then the weight of the superabsorbent polymer excluding the container was measured. The weight of the superabsorbent polymer only was divided by the volume of the superabsorbent polymer, i.e., 100 ml, thereby calculating an apparent density corresponding to the weight of the superabsorbent polymer per unit volume.

(5) CRC (Centrifugal Retention Capacity)

Centrifugal retention capacity (CRC) by absorption rate under no load was measured according to European Disposables and Nonwovens Association (EDANA) Standard EDANA WSP 241.3. $W_0$ (g, about 0.2 g) of the superabsorbent polymer was uniformly put in an envelope made of a non-woven fabric and sealed, and then soaked in a saline solution (0.9 wt % sodium chloride aqueous solution) at room temperature. After 30 minutes, the envelope was drained at 250 G for 3 minutes using a centrifuge, and then the weight $W_2$ (g) of the envelope was measured. Further, the same operation was conducted without using a superabsorbent polymer, and then the weight $W_1$ (g) at that time was measured. Using the obtained weights, CRC (g/g) was calculated according to the following Equation 3, thus confirming centrifugal retention capacity.

$$\text{CRC}(g/g) = \{[W_2(g) - W_1(g) - W_0(g)]/W_0(g)\} \quad [\text{Equation 3}]$$

TABLE 1

| | Content of EDTA-2Na in antimicrobial agent (parts by weight) | Agent for controlling particle size (parts by weight) | Flowability (s) | Bulk density (g/cm³) | Dust number |
|---|---|---|---|---|---|
| Reference Example 1 (antimicrobial agent only) | 1 | 0 | 7.3 | 0.84 | 18.4 |
| Reference Example 2 (antimicrobial agent only) | 0.5 | 0 | 6.2 | 0.89 | 20.8 |
| GS401N | — | — | 9.2 | 0.62 | 1.1 |
| Comparative Example 1 | 0.25 | 0 | 9.0 | 0.69 | 2.4 |
| Comparative Example 2 | 0.5 | 0 | 9.0 | 0.69 | 3.2 |
| Comparative Example 3 | 1.0 | 0 | 8.9 | 0.70 | 6.1 |
| Example 1 | 0.5 | 0.25 | 9.0 | 0.69 | 2.6 |
| Example 2 | | 0.5 | 9.0 | 0.69 | 1.9 |
| Example 3 | | 1.0 | 9.1 | 0.68 | 1.4 |
| Example 4 | | 1.5 | 9.3 | 0.68 | 1.3 |
| Example 5 | 0.8 | 0.5 | 9.1 | 0.69 | 1.9 |
| Example 6 | | 1.0 | 9.3 | 0.69 | 1.9 |
| Example 7 | | 1.5 | 9.3 | 0.67 | 1.4 |
| Example 8 | | 2.0 | 9.4 | 0.68 | 0.6 |

TABLE 1-continued

|  | Content of EDTA-2Na in anti-microbial agent (parts by weight) | Agent for controlling particle size (parts by weight) | Flow-ability (s) | Bulk density (g/cm³) | Dust number |
|---|---|---|---|---|---|
| Example 9 | 1.0 | 0.125 | 9.5 | 0.68 | 3.5 |
| Example 10 |  | 0.25 | 9.4 | 0.68 | 3.2 |
| Example 11 |  | 0.5 | 9.3 | 0.69 | 2.7 |
| Example 12 |  | 1 | 9.5 | 0.68 | 2.1 |
| Example 13 |  | 2 | 9.8 | 0.65 | 1.0 |

TABLE 2

|  | Incubation time | Measurement of antimicrobial efficiency | | CRC (g/g) |
|---|---|---|---|---|
|  |  | CFU/ml | log[CFU/ml] |  |
| Control | 0 h | 250,000 | 5.40 | — |
|  | After 12 h | 110,000,000 | 8.04 | — |
| Superabsorbent polymer only | After 12 h | 1,200,000 | 6.08 | 37.3 |
| Comparative Example 1 | After 12 h | 880,000 | 5.94 | 36.6 |
| Comparative Example 2 | After 12 h | 350,000 | 5.54 | 36.3 |
| Comparative Example 3 | After 12 h | 210,000 | 5.32 | 36.0 |
| Example 9 | After 12 h | 270,000 | 5.43 | 35.5 |
| Example 10 | After 12 h | 260,000 | 5.41 | 35.6 |
| Example 11 | After 12 h | 360,000 | 5.56 | 34.8 |
| Example 12 | After 12 h | 300,000 | 5.48 | 34.5 |
| Example 13 | After 12 h | 240,000 | 5.38 | 35.8 |

Referring to Tables 1 and 2, it was confirmed that the superabsorbent polymer compositions of the examples exhibited improved antimicrobial/deodorizing properties while maintaining centrifugal retention capacity at least equivalent to the comparative examples, by adding a specific amount of an agent for controlling a particle size to functional additives. Particularly, it can be seen that the examples of the present invention can remarkably reduce a dust value generated during the process, compared to the comparative examples, and thus can provide an antimicrobial superabsorbent polymer composition fulfilling both stability and processability.

Herein, since a direct cause of dust in the antimicrobial mixture is EDTA-2Na, the higher content may cause a dust problem, and thus in the case of Comparative Examples 1 to 3, when the content of EDTA-2Na was increased, a dust value increased.

To the contrary, in the case of Examples 1 to 13, even if the content of EDTA-2Na was increased, by adding a specific amount of an agent for controlling a particle size, a dust value could be relatively reduced compared to Comparative Examples 1 to 3. Furthermore, compared to the case of using the superabsorbent polymer only, the antimicrobial efficiency of the superabsorbent polymer using an antimicrobial agent described herein was maintained to be excellent.

The invention claimed is:

1. A superabsorbent polymer composition comprising:
superabsorbent polymer particles comprising a crosslinked polymer of water-soluble ethylenically unsaturated monomers including acid groups, wherein at least a part of the acid groups are neutralized; and
an antimicrobial agent,
wherein the antimicrobial agent includes a chelating agent including EDTA or an alkali metal salt thereof, a mixture of an organic acid and a silicate-based salt, and an agent for controlling a particle size of the antimicrobial agent,
wherein the organic acid is included in a content of 90 to 99.5 wt %, based on a total weight of the mixture of the organic acid and the silicate-based salt, and
wherein the mixture of the organic acid and the silicate-based salt is included in the content of 0.5 to 5 parts by weight, based on 100 parts by weight of the superabsorbent polymer particles.

2. The superabsorbent polymer composition according to claim 1, wherein the agent for controlling a particle size is included in a content of 0.1 to 5 parts by weight, based on 100 parts by weight of a sum of the chelating agent, and the mixture of the organic acid and the silicate-based salt.

3. The superabsorbent polymer composition according to claim 1, wherein the agent for controlling a particle size is one or more selected from the group consisting of mineral oil, natural oil, baby oil, and silicone oil.

4. The superabsorbent polymer composition according to claim 1, wherein the antimicrobial agent is included in a content of 0.1 to 5 parts by weight, based on 100 parts by weight of the superabsorbent polymer particles.

5. The superabsorbent polymer composition according to claim 1, wherein the chelating agent further comprises one or more selected from the group consisting of cyclohexane diamine tetraacetic acid, diethylene triamine pentaacetic acid, ethylene glycol-bis-(aminoethylether)-N,N,N'-triacetic acid, N-(2-hydroxyethyl)-ethylene diamine-N,N,N'-triacetic acid, triethylene tetraamine hexaacetic acid, and alkali metal salts thereof.

6. The superabsorbent polymer composition according to claim 1, wherein the chelating agent further comprises EDTA sodium salts of EDTA-2Na or EDTA-4Na.

7. The superabsorbent polymer composition according to claim 1, wherein the chelating agent is included in a content of 0.1 to 5 parts by weight, based on 100 parts by weight of the superabsorbent polymer particles.

8. The superabsorbent polymer composition according to claim 1, wherein the organic acid includes one or more selected from the group consisting of citric acid, fumaric acid, maleic acid, and lactic acid.

9. The superabsorbent polymer composition according to claim 1, wherein the silicate-based salt includes a salt in which a silicate anion, and a cation of an alkali metal or an alkali earth metal, are bonded.

10. The superabsorbent polymer composition according to claim 1, wherein the water-soluble ethylenically unsaturated monomers include one or more selected from the group consisting of anionic monomers, non-ionic hydrophilic group-containing monomers, and amino group-containing unsaturated monomers.

11. The superabsorbent polymer composition according to claim 1, further comprising a surface crosslink layer formed on the superabsorbent polymer particles.

12. The superabsorbent polymer composition according to claim 10, wherein the anionic monomers are one or more selected from the group consisting of acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloyl propane sulfonic acid, 2-(meth)acrylamid-2-methyl propane sulfonic acid, and salts thereof.

13. The superabsorbent polymer composition according to claim 10, wherein the non-ionic hydrophilic group-containing monomers are one or more selected from the group consisting of (meth)acrylamide, N-substituted (meth)acrylate, 2-hydroxyethyl (meth)acrylate, 2-hydroxypropyl (meth)acrylate, methoxy polyethylene glycol (meth)acrylate, and polyethylene glycol (meth)acrylate.

14. The superabsorbent polymer composition according to claim 10, wherein the amino group-containing unsaturated monomers are one or more selected from the group consisting of (N,N)-dimethylaminoethyl (meth)acrylate, (N,N)-dimethylaminopropyl (meth)acrylamide, and quaternarized products thereof.

15. The superabsorbent polymer composition according to claim 3, wherein the natural oil is corn oil or olive oil.

16. The superabsorbent polymer composition according to claim 1, wherein the superabsorbent polymer composition consists of the superabsorbent polymer particles and the antimicrobial agent,
  wherein an antimicrobial agent consists of a chelating agent including EDTA or an alkali metal salt thereof, a mixture of an organic acid and a silicate-based salt, and an agent for controlling a particle size of the antimicrobial agent, and
  wherein the agent for controlling a particle size consists of one or more selected from the group consisting of mineral oil, natural oil, baby oil, and silicone oil.

* * * * *